United States Patent [19]

Witiak et al.

[11] 4,213,998

[45] Jul. 22, 1980

[54] INHIBITION OF LIPOGENESIS

[75] Inventors: Donald T. Witiak, Columbus, Ohio; John B. Carr, Houston, Tex.; Harry J. Mersmann, Modesto, Calif.

[73] Assignee: Shell Oil Company, Houston, Tex.

[21] Appl. No.: 46,592

[22] Filed: Jun. 7, 1979

Related U.S. Application Data

[63] Continuation-in-part of Ser. No. 9,338, Feb. 5, 1979, abandoned, which is a continuation of Ser. No. 904,084, May 8, 1978, abandoned, which is a continuation of Ser. No. 811,647, Jun. 30, 1977, abandoned.

[51] Int. Cl.² ............................................. A61K 31/34
[52] U.S. Cl. .................................................... 424/285
[58] Field of Search ......................................... 424/285

[56] References Cited

U.S. PATENT DOCUMENTS

| | | | |
|---|---|---|---|
| 3,651,094 | 3/1972 | Libis et al. | 424/285 |
| 3,751,430 | 8/1973 | Libis et al. | 424/285 |
| 3,843,797 | 10/1974 | Habicht et al. | 424/285 |
| 3,920,820 | 11/1975 | Scherrer | 424/285 |

*Primary Examiner*—Stanley J. Friedman

[57] ABSTRACT

Lipogenesis in mammals is inhibited by benzofurancarboxylic acids substituted on the aromatic ring by one of certain moieties, and the 2,3-dihydro counterparts thereof.

1 Claim, No Drawings

INHIBITION OF LIPOGENESIS

This application is a continuation-in-part of application Ser. No. 9,338, filed on Feb. 5, 1979, now abandoned which was a continuation of application Ser. No. 904,084, filed on May 8, 1978, now abandoned, which was a continuation of application Ser. No. 811,647, filed on June 30, 1977, now abandoned.

DESCRIPTION OF THE INVENTION

It has been found that lipogenesis in mammals is inhibited by benzofurancarboxylic acids substituted on the aromatic ring by one of certain moieties, and the 2,3-dihydro counterparts thereof, all of these compounds being described by the formula:

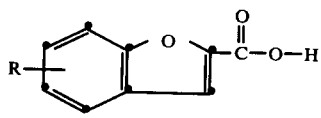

wherein R is cycloalkyl of from three to six carbon atoms; alkyl or alkoxy of from one to eight carbon atoms; or is phenyl, phenoxy, benzyl or benzoyl or any of these substituted by one of alkyl or alkoxy of from one to six carbon atoms, fluorine, chlorine, bromine, nitro, acetyl, acetoxy and hydroxy, with the proviso that R also can be chlorine substituted at the 7-position of the molecule. In these compounds, each aliphatic moiety may be of straight-chain or branched-chain configuration.

The dotted line between the carbon atoms at the 2- and 3-positions in the ring structure indicates that these carbon atoms may be linked by a double bond (i.e., the benzofuran subgenus) or by a single bond (i.e., the 2,3-dihydrobenzofuran subgenus).

Chirality exists in the 2,3-dihydro members, hence they can exist in two optical isomeric forms. None of the isomers has been separated, nor has the lipogenesis inhibition activity of any of the individual isomers been determined. The 2,3-dihydro species that have been prepared inhibit lipogenesis. Under the circumstances, the invention contemplates the furan subgenus, the 2,3-dihydrofuran subgenus, including the individual isomers of the latter subgenus, as well as mixtures thereof.

Generally speaking, acids of the furan subgenus can be prepared by hydrolysis of the corresponding ethyl esters, by the method of Kurkudar and Rao, Indian Acad. Sci., Section A, 58, 336 (1963), while acids of the 2,3-dihydrofuran subgenus can be prepared by reduction of the corresponding acids of the furan subgenus, through use of sodium/-mercury amalgam, according to the method of Fredga, Acta Chem. Scand., 9, 719 (1955).

The precursor ethyl esters of the furan subgenus can be prepared by condensation of the appropriate R-substituted salicylaldehyde with diethyl bromomalonate in the presence of anhydrous potassium carbonate, according to the methods of Kurkudar and Rao, and of Witiak, D.T., et al., Lipids, 11 (5), 384-391 (1976) and the references mentioned therein.

The precursor R-substituted salicylaldehydes can be prepared by treating the appropriate phenol with chloroform under strongly basic conditions, according to the Reimer-Tieman Reaction. (References cited in the Merck Index, 9th edition, page ONR-74; also, Russell, A. and Lockhart, L.B., Organic Synthesis, 22, 63 (1942)).

Many of the precursor phenols are known compounds; others can be prepared by conventional procedures.

Preparation of compounds of Formula I is illustrated in the following examples. In each case, the identities of the product, and of the precursor(s) involved, were confirmed by appropriate chemical and spectral analyses.

EXAMPLE 1

5-phenyl-2-benzofurancarboxylic acid (1)

22 g of phenylphenol was dissolved in 95% ethanol; a solution of 40 g of sodium hydroxide in 80 ml of water was rapidly added. The resulting solution was heated to 75°–80° C. and 20 ml of chloroform was added over a one-hour period, the mixture being gently refluxed. The mixture then was stirred for three hours, cooled and the ethanol and excess chloroform were evaporated under reduced pressure. The resulting residue was cooled and poured into cold water. The resulting mixture was acidified by slow addition of hydrochloric acid and extracted with ether. The solvent was evaporated from the extract under reduced pressure, the residue was poured in twice its volume of saturated sodium metabisulfite solution and the mixture was shaken vigorously for forty-five minutes. The resulting semisolid bisulfite addition compound was allowed to stand for one hour, filtered in the dark and washed with small portions of ethanol and ether to remove the phenol. The bisulfite addition compound was decomposed with dilute sulfuric acid, the mixture being warmed on a water-bath for thirty minutes. The cooled mixture was extracted with ether, dried ($Na_2SO_4$), and the solvent was evaporated under reduced pressure. The residue was treated with activated charcoal and recrystallized from ethanol/water to give 5-phenylsalicylaldehyde (1A), as yellow crystals, mp: 98°–99° C.

A mixture of 0.99 g of 1A, 0.96 g of diethyl bromomalonate and 1.25 g of anhydrous potassium carbonate in 20 ml of 2-butanone was refluxed for 10 hours. The solvent was evaporated under reduced pressure. The residue was cooled, poured into 100 ml of water and extracted with ether. The extract was washed with cold 5% sodium hydroxide solution and water and then concentrated under reduced pressure. The residue was recrystallized from ethanol to give ethyl 5-phenylbenzofuran-2-carboxylate (1B), as white crystals, mp: 109°–110° C.

A mixture of 1.3 g of Compound 1B and 50 ml of 10% alcoholic potassium hydroxide was refluxed for 4 hours. The solvent was evaporated under reduced pressure and the residue was washed with ether and dissolved in water. The basic solution was acidified with dilute hydrochloric acid and extracted with ether. The ether layer was extracted with dilute sodium bicarbonate solution. The aqueous extract was re-acidified with dilute hydrochloric acid and extracted with ether. The ether extract was dried ($Na_2SO_4$) and concentrated under reduced pressure. The residue was crystallized from ethanol to give 1, as white solid, mp: 220°–221° C.

EXAMPLE 2

2,3-dihydro-5-phenyl-2-benzofurancarboxylic acid (2)

5.0 g of 1 was mixed with 90 ml of 10% sodium hydoxide solution. Sodium amalgam (prepared from 1.5 g of sodium and 50 1 g of mercury) was added to the stirred mixture over a period of one hour. The mixture was then stirred for 24 hours and allowed to stand at room temperature for an additional 24 hours. The mercury was separated, and the solution was neutralized with dilute hydrochloric acid and extracted with ether. The extract was dried ($Na_2SO_4$) and concentrated under reduced pressure, and the residue was recrystallized from ethanol to give 2, as white crystals, mp: 186°–187° C.

EXAMPLES 3–8

By procedures similar to those described in Example 1, the following additional individual species of the benzofuran subclass of the class of compounds defined in Formula I were prepared from known phenols:

| Example No. | Compound No. | R (number indicating position on ring) | Melting Point (°C.) |
|---|---|---|---|
| 3 | 3 | 5-(1-methylpropyl) | 124–126 |
| 4 | 4 | 5-cyclohexyl | 203.5–206 |
| 5 | 5 | 6-phenoxy | 215–217 |
| 6 | 6 | 5-benzoyl | 195–198 |
| 7 | 7 | 5-hexyloxy | 147–149 |
| 8 | 8 | 5-benzyl | 229–231 |

EXAMPLE 9

4-phenoxy-2-benzofurancarboxylic acid (9)

9, mp: 215–217, was prepared by procedures similar to those described in Example 1, from the precursor salicyaldehyde prepared as follows:

14.0 g of meta-phenoxyphenol was dissolved in 700 ml of 95% ethanol. 468 g of sodium hydroxide was then added rapidly. The resulting suspension was heated to 70°–80° C. Then 558.7 g of chloroform was added, at such a rate that gentle reflux was maintained; the addition required 10 hours. The mixture then was stirred for 2 hours at 75°–80° C., held at room temperature overnight and filtered. The solid product was dissolved in 1000 ml of water. The solution was acidified to pH=2 with concentrated hydrochloric acid, then was extracted with ether. The ether layer was dried ($MgSO_4$) and concentrated. The residue was extracted with hot petroleum ether. The extract was dried ($Na_2SO_4$) and concentrated to give an oil, which was wet column chromatographed over silica gel, using first a 9/1 v/v mixture, then a 4/1 v/v mixture of petroleum ether and ether as eluent. The fourth fraction obtained, after removal of the solvents, was identified as 2-hydroxy-6-phenoxybenzaldehyde.

EXAMPLE 10

5-(4-acetylphenyl)-2-benzofurancarboxylic acid (10)

12.2 g of acetyl chloride was added to a mixture of 10.3 g of 1B, and 120 ml of carbon disulfide, then 21.8 g of anhydrous aluminum chloride was added in portions to the stirred mixture. The mixture then was stirred at room temperature for 2.5 hours, the temperature rising to 32° C. The mixture was poured into 1 liter of ice water, and stirred for 30 minutes, and the solution was extracted with ether. The extract was dried ($MgSO_4$) and concentrated. The residue was washed with ether and dissolved in 100 ml of chloroform. The solution was treated with activated charcoal, and 100 ml of hexane was added. The resulting solution was concentrated to about 100 ml and cooled to give ethyl 5-(4-acetylphenyl)-benzofuran-2-carboxylate (10A), mp: 105°–107° C.

10A was treated with potassium hydroxide in ethanol to give 10, mp: 264°–266° C.

EXAMPLE 11

5-(4-(acetyloxy)phenyl)-2-benzofurancarboxylic acid (11)

2 ml of trifluoroacetic acid and 92 ml of 30% hydrogen peroxide solution were added to a mixture of 13 g of 10 in 300 ml of acetic acid. The mixture was heated at 70°–75° C. for 10 hours, then was cooled in a refrigerator. The solid that formed was collected and dried. The acetic acid solution was poured into 3.6 liters of ice water. The solid that formed was collected and dried ($P_2O_5$). The two solids were combined and dissolved in 150 ml of tetrahydrofuran. The solution was filtered, concentrated to 20 ml and chilled. The solid that formed was collected, dried under reduced pressure, and recrystallized from tetrahydrofuran to give 11, mp: 251°–254° C.

EXAMPLE 12

5-(4-chlorophenyl)-2-benzofurancarboxylic acid (12)

A mixture of 6.2 g of 10A, 100 ml of ethanol and 200 ml of tetrahydrofuran was heated to 60°–70° C. A solution of 1.53 g of hydroxylamine hydrochloride and 1.16 g of sodium carbonate in 20 ml of water was added. The mixture was heated for 3 hours at 60°–70° C. The resulting solid was collected, washed with water, then ethanol, and extracted with methylene chloride. The solvent was evaporated from the extract under reduced pressure to give ethyl 5-(4-(1-(hydroxyimino)ethyl)-phenyl)-2-benzofurancarboxylate (12A), mp: 220°–222° C.

56.5 g of phosphorus pentachloride was added in portions to a solution of 55.0 g of 12A in 1 liter of chloroform, and the mixture was stirred at room temperature for 16 hours. The solvent was evaporated under reduced pressure. The residue was suspended in 4 liters of water, the mixture was stirred vigorously for 30 minutes and filtered. The solid was extracted with chloroform. The extract was washed, successively, with water, saturated sodium bicarbonate solution, and water, then was filtered through celite (to break the emulsion). The filtrate was dried ($MgSO_4$) and the solvent was evaporated under reduced pressure. The residue was triturated with ether. The ether phase was separated, then concentrated to about half its volume under reduced pressure and allowed to stand over a weekend. The solid which formed was collected and dissolved in 400 ml of chloroform. The solution was filtered over charcoal, and diluted with 400 ml of hexane. The resulting solid was collected and dry column chromatographed over silica gel, using a 1/9 v/v mixture of tetrahydrofuran and chloroform as eluent. After removal of the solvents, the appropriate fractions were combined and extracted with tetrahydrofuran. The solvent was evaporated under reduced pressure and the residue was triturated with ether. The resulting solid was collected and dried under reduced pressure to give ethyl 5-(4-(acetylamino)phenyl)-2-benzofurancarboxylate (12B), mp: 174°–176° C.

A mixture of 3.0 g of 12B, 50 ml of 6 N hydrochloric acid and 50 ml of ethanol was stirred and refluxed for 5 hours. The solution was concentrated to about half its volume, the solid that formed was collected, and dissolved in chloroform containing some triethylamine. The solution was washed with water, dried (MgSO4) and filtered. The solvent was evaporated from the filtrate under reduced pressure. The residue was dry column chromatographed over silica gel, using a 1/9 v/v mixture of tetrahydrofuran and chloroform as eluent. The solvents were evaporated, the appropriate sections were combined and extracted with chloroform. The extract was filtered and the solvent was evaporated under reduced pressure. The residue was refluxed in petroleum ether for 8 hours. The mixture was filtered and the filtrate placed in a freezer overnight. The solid that formed was collected and dried to give ethyl 5-(4-aminophenyl)benzofuran-2-carboxylate (12C), mp: 95°–97° C.

A solution of 6.9 g of sodium nitrite in 40 ml of water was added drop-by-drop to a stirred mixture of 30 g of 12C and 160 ml of 6 N hydrochloric acid, the rate of addition being adjusted to maintain the temperature of the reaction mixture at 0°–5° C. The mixture was stirred for 1 hour at 0°–5° C., then added with vigorous stirring, to 50 ml of 20% aqueous cuprous chloride heated to 70° C. The resulting mixture was heated to 70° C., then allowed to cool. The solid was collected, washed with water, dried ($P_2O_5$, reduced pressure) and dissolved in tetrahydrofuran. The solution was suspended on 75 g of silica gel and dry column chromatographed, using chloroform as eluent. The product was removed from the combined appropriate fractions with tetrahydrofuran. The solvent was evaporated ad the residue was dried (drying pistol, $P_2O_5$, refluxing acetone) to give ethyl 5-(4-chlorophenyl)benzofuran-2-carboxylate (12 D), mp 108°–110° C.

12 D was treated with potassium hydroxide to give 12, mp: 254°–256° C.

EXAMPLES 13–15

The following three individual species were purchased:

| Example No. | Compound No. | R |
|---|---|---|
| 13 | 13 | 7-methoxy |
| 14 | 14 | 6,7-dimethoxy |
| 15 | 15 | 7-chloro |

EXAMPLE 16

5-(4-hydroxyphenyl)-2-benzofurancarboxylic acid (16)

A mixture of 10.4 g of 11 and 7.2 g of potassium hydroxide in 170 ml of ethanol was refluxed for 2 hours. The solvent was evaporated under reduced pressure. The residue was mixed with 200 ml of water, and the mixture was acidified to pH=2 with concentrated hydrochloric acid, stirred for 30 minutes and filtered. The solid was washed with water, dried under reduced pressure and mixed with tetrahydrofuran. The mixture was refluxed and filtered. The filtrate was concentrated, the residue was washed with ether and mixed with tetrahydrofuran. The mixture was filtered, the filtrate was concentrated to about one-fourth its volume and triturated with ether. The resulting solid was collected and dried under reduced pressure to give 16, mp: 297°–300° C.

EXAMPLE 17

5-(4-methoxyphenyl)-2-benzofurancarboxylic acid (17)

16.6 g of methyl iodide and 17.8 g of potassium carbonate were added to a mixture of 20.0 g of 16, 400 ml of dimethyl sulfoxide and 150 ml of acetone. The mixture was heated at 65°–70° C. for 3 hours. A further 16.5 g of methyl iodide and 8.9 g of potassium carbonate were added, and the heating was continued for 4 hours. The mixture was poured into ice water. The resulting solid was collected, washed with water and dried ($P_2O_5$, reduced pressure). The solid was mixed with tetrahydrofuran, the mixture was filtered, the filtrate was dried ($NA_2SO_4$) and concentrated to a small volume. The resulting solid was separated and recrystallized from 2/1 v/v mixture of chloroform and hexane. The product was dry column chromatographed, using chloroform as eluent. The solvent was evaporated, the appropriate fractions were extracted with chloroform and the solvent was evaporated from the extract. The residue was washed with ether and dried under reduced pressure to give methyl 5-(4-methoxyphenyl)-2-benzofurancarboxylate, 17 A, mp: 160°–162° C.

17 A was treated with potassium hydroxide to give 17, mp: 181°–184° C.

EXAMPLES 18–24

By the general procedure described in Example 2, the fllowing further individual species or the 2,3-dihydro subgenus of Formula I were prepared from the corresponding individual species of the furan subgenus:

| Example No. | Compound No. | R | Melting Point (°C.) |
|---|---|---|---|
| 18 | 18 | 5-(1-methylpropyl) | 91–94 |
| 19 | 19 | 5-cyclohexyl | 153–155 |
| 20 | 20 | 5-benzyl | 111–112 |
| 21 | 21 | 5-hexyloxy | 91–93 |
| 22 | 22 | 6-phenoxy | 131–133 |
| 23 | 23 | 4-phenoxy | 123–125 |
| 24 | 24 | 5-(4-chlorophenyl) | 147–149 |

Acids of Formula I have been found to inhibit lipogenesis in tissues of mammals. The manner in which they cause this effect is not known with certainty; it is believed that they interfere with the synthesis of fatty acids in the tissues. Their effectiveness for this purpose has been ascertained by immersing sales of swine adipose tissue in a liquid medium containing radioactive glucose and the test chemical for a period of time, then isolating the lipid from the treated tissue and determining the incorporation of the radioactive carbon into lipid by means of scintillation counting techniques. These tests were conducted in swine adipose tissues because in swine, the primary site of lipogenesis—i.e., fatty acid synthesis—appears to be adipose tissue.

Described in more detail, the tests were conducted according to the following general procedure:

150 milligrams of slices of swine adipose tissue were incubated at 37° C. for 2 hours with shaking in 3 milliliters of Krebs-Ringer bicarbonate solution containing one-half the normal calcium ion concentration, 60 micromoles of glucose, 0.5 micro-Curie of glucose-$U^{14}C$, and 300 microunits of insulin, and 5% dimethylsulfoxide (DMSO). The test compounds were added as a solution or suspension in DMSO and were present at a concentration of 100 micrograms per milliliter of the incubation mixture.

The incubation was terminated by addition of 0.25 milliliter of 1 N sulfuric acid. The resulting mixture was extracted with a total of 25 milliliters of chloroform/methanol (2:1 v/v). The extracts were washed according to Folch et al. (J. Biol. Chem. 226, 497–509, (1957)), air dried, and counted in a liquid scintillation counter with 15 milliliters of counting fluid (two parts toluene containing 0.4% w/v New England Nuclear Omnifluor/1part Triton X-100). The tests were conducted in triplicate and were accompanied by control tests in which all ingredients, proportions and conditions were the same except that no test compound was included. From the data obtained were calculated the precent inhibition of lipid synthesis by the test compounds in each case. The data obtained from the tests are set out in Table 1, as the percent inhibition of lipogenesis compared to the results obtained in the control tests wherein only the test compound was omitted.

Table 1

| Compound No. | Percent Inhibition |
|---|---|
| 1 | 49 |
| 2 | 50 |
| 3 | 64 |
| 4 | 91 |
| 5 | 86 |
| 6 | 44 |
| 7 | 78 |
| 8 | 87 |
| 9 | 83 |
| 10 | 41 |
| 11 | 80 |
| 12 | 55 |
| 13 | 22 |
| 14 | 24 |
| 15 | 59 |
| 16 | 30 |
| 17 | 56 |
| 18 | 35 |
| 19 | 72 |
| 20 | 40 |
| 21 | 49 |
| 22 | 62 |
| 23 | 27 |
| 24 | 56 |

The acids of Formula I can be used to control lipogenesis in mammals such as, for example, pets, animals in a zoo, livestock, furbearing animals and domestic animals, including, but not limited to dogs, cats, mink, sheep, goats, swine, cattle, horses, mules and donkeys. The effect is obtained by administering an effective amount of one or a mixture of two or more of the acids orally or parenterally to the animal. They may be administered as such, or as an active ingredient of a conventional pharmaceutical formulation. They may be administered orally by any convenient means. Thus, they may be orally administered as a drench, by intubation, in the animal's food and water, in a food supplement or in a formulation expressly designed for administration of the drug. Suitable formulations include solutions, suspensions, dispersions, emulsions, tablets, boluses, powders, granules, capsules, syrups and elixirs. For parental administration, they may be in the form of a solution, suspension, dispersion or emulsion. They can be administered in the form of an implant or other controlled sustained release formulation. Inert carriers, such as ne or more of water, edible oil, gelatin, lactose, starch, magnesium sterate, talc or vegetable gum can be used. The dosage of the acid needed to inhibit lipogenesis will depend upon the particular acid used, and the particular animal being treated. However, in general, satisfactory results are obtained when the acids are administered in a dosage of from about 1 to about 400 milligrams per kilogram of the animal's body weight. The acid can be administered in a single dose or in a series of doses in the same day, or over a period of days. For any particular animal, a specific dosage regimen should be adjusted according to the individual need, the particular ester(s) used as the inhibitor, and the professional judgement of the person administering or supervising the administration of the inhibitor. It is to be understood that the dosages set forth herein are exemplary only, and that they do not, to any extent, limit the scope or practice of the invention.

The invention claimed:

1. A method of inhibiting lipogenesis in a mammal, which comprises administering to a mammal, orally or parenterally, an effective amount of a compound of the formula

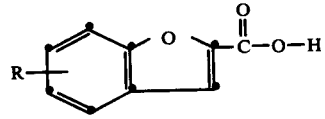

wherein R is cycloalkyl of from three to six carbon atoms; alkyl or alkoxy of from one to eight carbon atoms; or is phenyl, phenoxy, benzyl or benzoyl or any of these substituted by one of alkyl or alkoxy of from one to six carbon atoms, fluorine, chlorine, bromine, nitro, acetyl, acetoxy and hydroxy, with the proviso that R also can be chlorine substituted at the 7-position of the molecule.

* * * * *